US012478748B2

(12) United States Patent
Rawert et al.

(10) Patent No.: US 12,478,748 B2
(45) Date of Patent: Nov. 25, 2025

(54) AEROSOL DELIVERY OF AT LEAST TWO LIQUID COMPOSITIONS

(71) Applicant: INVOX BELGIUM NV, Diepenbeek (BE)

(72) Inventors: Juergen Rawert, Cologne (DE); Frank Bartels, Hattingen (DE); Steven Dudley, Brighton (GB)

(73) Assignee: INVOX BELGIUM NV, Diepenbeek (BE)

( * ) Notice: Subject to any disclaimer, the term of this patent is extended or adjusted under 35 U.S.C. 154(b) by 727 days.

(21) Appl. No.: 17/907,549

(22) PCT Filed: Mar. 29, 2021

(86) PCT No.: PCT/EP2021/058109
§ 371 (c)(1),
(2) Date: Sep. 28, 2022

(87) PCT Pub. No.: WO2021/198154
PCT Pub. Date: Oct. 7, 2021

(65) Prior Publication Data

US 2023/0218837 A1 Jul. 13, 2023

Related U.S. Application Data

(60) Provisional application No. 63/002,836, filed on Mar. 31, 2020.

(30) Foreign Application Priority Data

Mar. 31, 2020 (EP) .................................... 20167140

(51) Int. Cl.
*A61M 15/00* (2006.01)
*A61K 31/357* (2006.01)
(Continued)

(52) U.S. Cl.
CPC ....... *A61M 15/0003* (2014.02); *A61K 31/357* (2013.01); *A61K 31/407* (2013.01);
(Continued)

(58) Field of Classification Search
CPC .... A61M 11/00–08; A61M 15/00–085; A61M 2205/8281; A61M 2202/0468;
(Continued)

(56) References Cited

U.S. PATENT DOCUMENTS

2009/0216183 A1 8/2009 Minotti

FOREIGN PATENT DOCUMENTS

EP 0627230 B1 2/2000
EP 1747035 B1 8/2011
(Continued)

OTHER PUBLICATIONS

Written Opinion of International Application No. PCT/EP2021/058109, Jun. 2, 2021, 11 pages.
(Continued)

*Primary Examiner* — Rachel T Sippel
*Assistant Examiner* — Jacqueline M Pinderski
(74) *Attorney, Agent, or Firm* — Morgan, Lewis & Bockius LLP

(57) ABSTRACT

The invention relates to the field of inhalation methods and inhalation devices for liquids. In particular, the invention relates to an inhalation method using an inhalation device adapted to separately eject at least two liquid compositions each having different properties, and to a method for the generation of an aerosol of at least two medicinal formulations by means of such inhalation device.

19 Claims, 1 Drawing Sheet

(51) Int. Cl.
*A61K 31/407* (2006.01)
*A61K 31/538* (2006.01)

(52) U.S. Cl.
CPC ....... *A61K 31/538* (2013.01); *A61M 15/0065* (2013.01); *A61M 2205/8281* (2013.01)

(58) Field of Classification Search
CPC ......... A61M 2205/3331; A61K 31/357; A61K 31/407; A61K 31/538
See application file for complete search history.

(56) References Cited

FOREIGN PATENT DOCUMENTS

| | | | | | |
|---|---|---|---|---|---|
| JP | 2007-524350 | A | | 8/2007 | |
| JP | 2019-112434 | A | | 7/2019 | |
| JP | 2020-502121 | A | | 1/2020 | |
| RU | 2376040 | C1 | | 12/2009 | |
| WO | 9114468 | A1 | | 10/1991 | |
| WO | 0204055 | A1 | | 1/2002 | |
| WO | WO-2005107837 | A1 | * | 11/2005 | ......... B05B 11/1015 |
| WO | 2018197730 | A1 | | 11/2018 | |
| WO | 2018234525 | A1 | | 12/2018 | |
| WO | 2020030682 | A1 | | 2/2020 | |

OTHER PUBLICATIONS

Office Action dated Apr. 30, 2025, issued in counterpart Japanese Patent Application No. 2022-570425 (5 pages).
Office Action dated Aug. 7, 2024, issued in counterpart Russian Patent Application No. 2022122215/14(047255) (35 pages).
Office Action dated Apr. 21, 2025, issued in counterpart Taiwan Patent Application No. 11420408350 (2 pages).
Contini, C. et al., "A new pharmacological approach based on remdesivir aerosolized administration of SARS-CoV-2 pulmonary inflammation: A possible and rational therapeutic application," Medical Hypothesis 144 (May 24, 2020) (9 pages).
Sun, D. "Remdesivir for Treatment of COVID-19: Combination of Pulmonary and IV Administration May Offer Additional Benefit," The AAPS Journal (May 26, 2020) 22:77 (pp. 1-6).

* cited by examiner

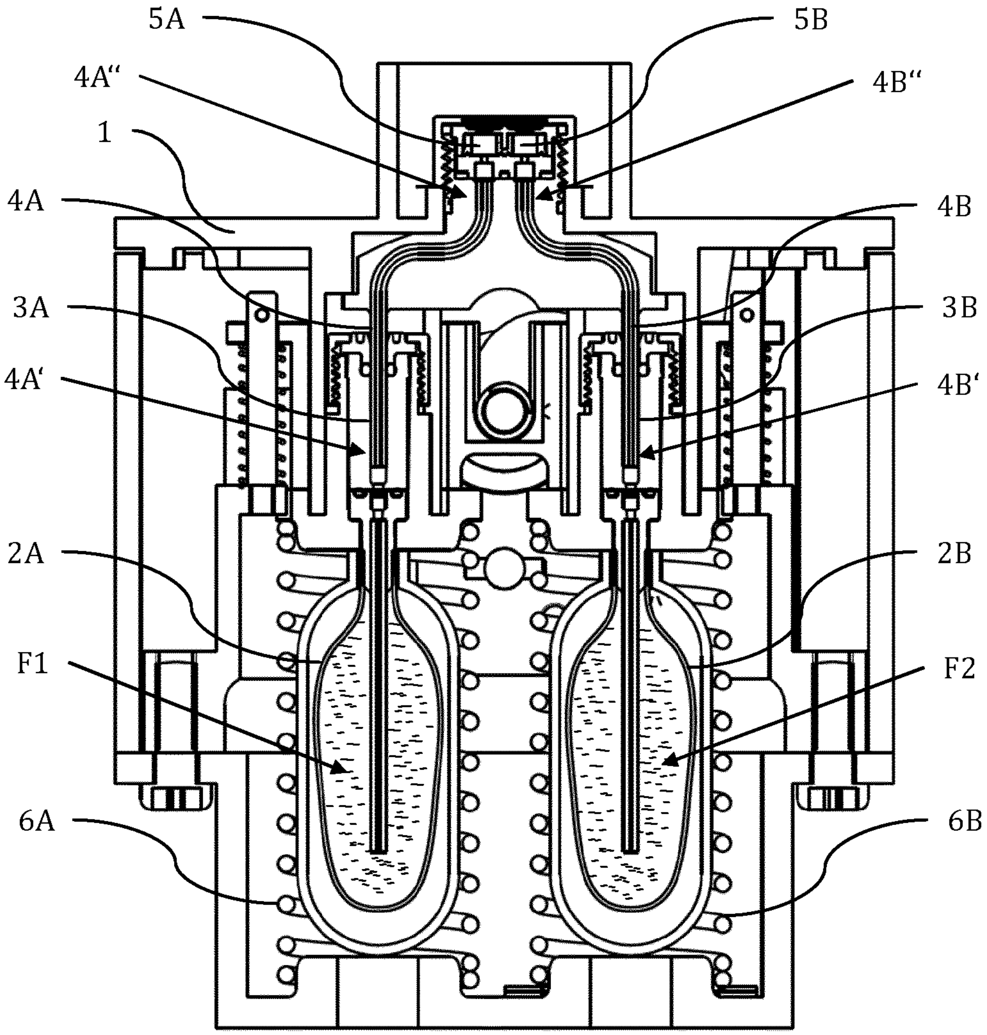
5A
5B
4A"
4B"
1
4A
4B
3A
3B
4A'
4B'
2A
2B
F1
F2
6A
6B

AEROSOL DELIVERY OF AT LEAST TWO LIQUID COMPOSITIONS

CROSS REFERENCE TO RELATED APPLICATIONS

This application is a United States National Stage Application filed under 35 U.S.C. § 371 claiming the benefit of PCT Application No. PCT/EP2021/058109, filed on Mar. 29, 2021, which claims priority to and the benefit of U.S. Provisional Application Ser. No. 63/002,836, filed on Mar. 31, 2020, and EP Application Serial No. 20167140.1, filed on Mar. 31, 2020, all of which are hereby incorporated by reference herein in their entireties.

FIELD OF THE INVENTION

The present invention relates to the field of inhalation devices for medically active liquids. In particular, the invention relates to an inhalation device for the generation of an aerosol, the device comprising at least a first reservoir and a second reservoir containing a first liquid composition and a second liquid composition.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e., small liquid droplets embedded in a gas. Such an inhalation device is known, for example from the document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle. A pumping unit is defined as a unit or device component capable of moving or compressing a fluid material and that comprises at least one pumping chamber, and optionally further comprises auxiliary components as well, such as a body, interfaces, and the like. By means of the pumping unit, the liquid is drawn in a discrete amount, i.e., not continuously, from the reservoir, and fed to the nozzle. The pumping unit works without propellant and generates pressure mechanically.

A known embodiment of such an inhalation device is presented in document WO 91/14468 A1. In such a device, the pressure in the pumping chamber which is connected to the housing is generated by movement of a movable hollow piston. The piston is moveably arranged inside the immobile pumping chamber. The (upstream arranged) inlet of the hollow piston is fluidically connected to the interior of the reservoir (reservoir pipe section). Its (downstream arranged) tip leads into the pumping chamber. Furthermore, a check valve that inhibits a back flow of liquid into the reservoir is arranged inside the tip of the piston.

For filling the piston, the same is directly connected with its upstream end to the reservoir. By pulling out the piston of the pumping chamber, its interior volume is enlarged, such that an increasing relative negative pressure (i.e., partial vacuum) is built up inside the pumping chamber. This pressure propagates through the hollow piston into the reservoir, such that liquid is sucked from the same into the piston. At the same time, said valve opens at its tip, since the pressure inside the reservoir is higher than inside the (yet empty) pumping chamber. The pumping chamber is being filled. At the same time, a spring is loaded, and locked at the motion's end when the movable piston has reached its lower dead center and the pumping chamber is filled.

The spring can be manually unlocked. The stored energy is then abruptly released. The piston is again pushed in the direction of the pumping chamber and into the same, thus decreasing its interior volume. The aforementioned check valve is now closed, such that a growing pressure builds up inside the pumping chamber, since the liquid is inhibited from flowing back into the reservoir. Eventually, this pressure results in ejection of the liquid from the nozzle which is arranged at the downstream end of the pumping chamber.

In order to face the risk of a reverse flow of already ejected liquid or even outside air, a further check valve, subsequently being called outlet valve, can be arranged at the downstream end of the pumping chamber just before the nozzle, allowing emitted liquid to pass, but blocking incoming gas.

The piston is arranged inside the pressure spring, which is designed as helical spring, thus limiting its outside diameter. Also because of the typically small volume (e.g., 15 μl), the piston is designed with a thin interior (and often also exterior) diameter.

This typically small inner diameter of the movable piston (e.g., 0.3 to 1.0 mm), together with a small size of the check valve being arranged within, is a drawback of the described construction. The small diameter results in a high flow resistance, such that in particular, media of higher viscosities flow into and through the piston only very slowly. In other words, the described construction is suitable especially for low-viscosity (aqueous) liquids and for emitting low doses thereof. Furthermore, fabrication of a sufficiently tight check valve of small diameter is difficult.

Another disadvantage of the described solution is that only one type of liquid can be emitted at a time, i.e., depending on the content of the reservoir. If another liquid shall be aerosolized, the reservoir must be exchanged, and the nozzle must be cleaned from remnants of the previous liquid before the inhalation device can be used again.

From document EP 1 747 035 B1, an inhalation device is known which is based on the technique described above, but which comprises two separate reservoirs that are connected via two separate pumping mechanisms to two individual ejection nozzles. These nozzles can form two individual sprays consisting of said two liquids, or they can form a single spray that consists of these two liquids. However, the aforementioned drawbacks still apply. Furthermore, the inhalation device contains only one unit (e.g., a spring) that serves as the potential energy source for both reservoirs and pumping mechanisms. As a consequence, the two liquids to be dispensed must have similar properties, e.g., viscosities, as the force that will expel the two liquids will be the same.

Inhalation therapies of more than one drug are also known. In particular, triple combination therapies of a long-acting muscarinic antagonist ("LAMA"), a long-acting beta agonist ("LABA"), and an inhaled corticosteroid ("ICS") have been developed to treat patients with chronic obstructive pulmonary disease ("COPD"). Typically, the LAMA and LABA components are aqueous soluble, whereas the ICS component is soluble in organic solvents and insoluble in aqueous solution. Therefore, patients would need to use two to three different inhalers to dispense the components in liquid form as combining all three components into one solution is not possible without precipitation of at least one of the components. Alternatively, therapies combined in one device have been limited to dry powder or powder suspensions due to the incompatibility of triple solution formulations of LAMA+LABA+ICS.

It is an object of the present invention to provide an improved method for delivering liquid solutions having different properties and/or incompatible ingredients to a patient by inhalation that overcomes one or more of the disadvantages of currently known inhalation therapies. It is a further object to provide an inhalation device that enables such improved delivery method. Further objects of the invention will be clear on the basis of the following description of the invention, examples and claims.

SUMMARY OF THE INVENTION

In a first aspect, the invention relates to an inhalation device for the generation of an aerosol, the device comprising at least a first reservoir and a second reservoir containing a first liquid composition and a second liquid composition, wherein the inhalation device is a pump-actuated inhaler adapted to release upon actuation of a first potential energy storage unit and a second potential energy storage unit a metered dose of the first liquid composition and the second liquid composition from the first reservoir and the second reservoir through a first exit area and a second exit area. In another aspect, the present invention provides for a first reservoir and a second reservoir adapted for use with an inhalation device as defined in the embodiments described herein.

In a further aspect, the invention relates to an inhalation device according to the first aspect of the invention and as defined in the embodiments described herein, for use in the treatment or prevention of a disease or condition, in some embodiments a lung disease or condition. In yet a further aspect, the invention provides an improved method of delivering at least two liquid compositions to a subject according to which an inhalation device as described above is used for the administration of a first liquid composition and a second liquid composition having different properties and/or incompatible ingredients. In yet a further aspect, the invention provides a method of treating a subject which is based on such improved method of delivering at least two liquid compositions.

DETAILED DESCRIPTION OF THE INVENTION

The objects are solved by the subject-matter of the independent claims. Advantageous embodiments are described in the dependent claims, the subsequent description, as well as the accompanying figures.

Introductorily, some definitions of terms are given which are used throughout the description and claims. The definitions should be used to determine the meaning of the respective expressions unless the context requires a different meaning.

An “inhaler” or “inhaler device” or “inhalation device” is a device which is configured and adapted for the generation of an inhalable mist, vapor, or spray.

The term “about” or the like in connection with an attribute or value includes the exact attribute or precise value, as well as any attribute or value typically considered to fall within the normal or accepted variability associated with the technical field, and methods of measuring or determining said attribute or value.

“Atomization” and “nebulization” in the context of inhalers means the generation of fine, inhalable droplets of a liquid. The typical dimensions of atomized droplets are in the range of several microns.

An “aerosol” is a dispersion of a solid or liquid phase in a gas phase. The dispersed phase, also termed the discontinuous phase, is comprised of multiple solid or liquid particles. The aerosol generated by the inhalation device of the invention is a dispersion of a liquid phase in the form of inhalable liquid droplets in a gas phase which is typically air. The dispersed liquid phase may optionally comprise solid particles dispersed in the liquid.

A “cartridge” is a unit that houses one or more reservoirs that may be removed from the device and replaced when the reservoirs are empty. For example, a cartridge may house one reservoir containing one liquid composition. Alternatively, the cartridge may house at least two reservoirs, each containing a liquid composition, in one unit.

An “exit area” is a location where liquid exits the inhaler device upon actuation of the device. Multiple exit areas may be included in a single nozzle unit. Alternatively, each exit area may be included in its own separate nozzle unit. Each exit area may have one or more channels to eject a liquid composition from the device. For example, an exit area may only comprise one channel or may comprise at least two channels.

A “liquid” is a fluid material capable of altering its shape to that of a container which holds the liquid but retains a nearly constant volume independent of pressure. A liquid may represent a monophasic liquid solution or a dispersion with a continuous liquid phase and a dispersed phase which may or may not be liquid.

A “plurality” means two or more.

“Interior” means inside, but also, oriented towards the inside; “Exterior” means outside, but also, oriented towards the outside.

A “nozzle” is a unit that serves for the atomization/nebulization of liquid. Generally, the term means the unit in its entirety. However, a nozzle can comprise one or multiple sets of individual, identical or different sub-units. A nozzle may have a plurality of ejection channels for emitting the liquid compositions described herein.

The “main axis” of a nozzle is its central axis parallel or collinear to the direction into which the bulk of the emitted aerosol travels after leaving the nozzle.

The “ejection trajectory” is an imaginary and relatively straight line that starts at the end of an ejection channel. It resembles the initial travel path of a liquid emitted from the ejection channel when the inhalation device is operated. It is clear that the nozzle (and the entire inhalation device) must be adapted and configured by means of e.g., a suitable channel geometry and a sufficiently high pressure such that the emitted liquid can be provided in said straight line and with a sharp stream.

Where two or more ejection trajectories intersect, a “collision point” is formed.

The term “metered dose” refers to the amount, for example as defined in terms of volume (e.g., μL, microliter), of liquid composition that is releasable by the inhalation device as a result of a single (one) actuation of the device.

The term “a single dose” in reference to a composition refers to the complete amount of the composition administered to a subject in a dosing event, and which is pharmacologically active which is administered as part of a dosing regimen. As understood herein, a single dose may be administered to a subject, via a single (one) actuation of the inhalation device; alternatively, it may also be administered over a plurality of actuations of the inhalation device, for example 2, or 3, or 4 actuations of the device, and in accordance with the prescribed usage, whereby the metered doses released per individual actuation combine to provide the required single dose.

The term "comprising" and related terms "comprise" or "comprises" would be understood as meaning that features additional to the features prefaced by the term may be present. Conversely, the term "consists" and related terms would be understood as meaning that no other features, other than those prefaced by the term are present, and if present, only in trace or residual amounts such as to confer no technical advantage or relevance in respect of the object of the invention.

Further definitions are provided in the subsequent description.

In a first aspect, the invention relates to an inhalation device for the generation of an aerosol of at least two liquid compositions, the device comprising at least a first and second reservoir containing at least a first and a second liquid composition, wherein the inhalation device is a pump-actuated inhaler adapted to release upon actuation a metered dose of the first liquid composition from the first reservoir and a metered dose of the second liquid composition from the second reservoir, wherein the first and second reservoir for storing the first and second liquid composition are fluidically connected to at least a first and second pumping chamber for generation of a first pressure inside said first pumping chamber and a second pressure inside said second pumping chamber, a first and second riser pipe, each of which can be received with a reservoir-facing, interior end in said first and second pumping chamber, wherein the interior volume of the first and second pumping chamber is changeable by means of relative motion of the first and second pumping chamber to the first and second riser pipe, at least a first exit area and a second exit area adapted to separately eject the first and second liquid composition from the inhalation device, a first potential energy storage unit coupled with one end of the first pumping chamber, and a second potential energy storage unit coupled with one end of the second pumping chamber.

The inhalation device according to the invention serves for the generation of an aerosol of at least two liquid compositions (e.g., a first liquid composition and a second liquid composition), in particular, of such aerosols which can be inhaled by a subject, e.g., a warm-blooded animal or human, especially a human subject, in need thereof.

Preferably, the inhalation device is suited to be hand-held and/or portable and may also be used by the individual subject themselves, following prescribed instructions. In some embodiments, the first reservoir and the second reservoir are incorporated into a single cartridge unit or the first reservoir is incorporated into a first cartridge unit and the second reservoir is incorporated into a second cartridge unit. Such cartridge unit(s) may be removed from the device and replaced when the reservoirs are empty after use.

The inhalation device is pump-actuated inhaler which as understood herein is an inhalation device comprising at least two mechanically driven pump devices or units that are each capable of displacing or compressing a liquid and/or fluid, such as a first liquid composition and a second liquid composition each having different properties and different active ingredients, additives, and/or excipients according to the present invention. In one embodiment of the invention, the pump-actuated inhaler is a piston-pump actuated inhaler having at least two piston-pump systems and at least two potential energy storage units each coupled to the piston-pump systems.

The pump-actuated inhaler may comprise at least two pump devices or units, each coupled to a separate potential energy storage unit, which generate a desired pressure for releasing at least two compositions having different properties and active ingredients, additives, and/or excipients, such as in the present aspect, through a first exit area and a second exit area, generating at least two aerosol streams. In some preferred embodiments, the at least two aerosol streams are separated upon injection to prevent undesirable chemical interactions or precipitation of the active ingredients, additives, and/or excipients. By means of the at least two pumping units, each of the first liquid composition and second liquid composition is drawn in a discrete amount, i.e., not continuously, from the first reservoir and the second reservoir, and fed to the first exit area and the second exit area. The at least two pumping units work without propellant and generate pressure mechanically. The at least two pump units or devices each preferably comprise of a pumping chamber, and a means for the storage of potential energy, each device being coupled to the pumping chamber and being lockable in a loaded position, wherein upon unlocking, the stored energy is transformable into a motion of the pumping chamber. The inhaler device comprises at least two potential energy storage units comprising, such as, for example, a spring, a gas, or a magnetic force. Because each pump unit is coupled to a separate potential energy storage unit, each pump unit may be configured to expel each liquid composition with different forces or different volumes, to compensate for any differences in properties (e.g., viscosities) of the individual liquid compositions to be dispensed.

In specific embodiments, the at least two, or more specifically, the two potential energy storage units may each be in the form of a spring, wherein each of the at least two, or more specifically, two springs, may have the same or a different spring rate (k), preferably a different spring rate, typically selected within the range of from about 50 N/m (Newton/meter) to about 5.000 (five thousand) N/m, such as from about 100 N/m to about 2.000 N/m, or from about 150 N/m to about 1.500 N/m.

In further specific embodiments, the two springs may produce the same or a different force typically ranging from about 5 N to about 200 N (Newton), or from about 10 N to about 100 N, or from about 20 N to about 80 N, or from about 30 N to about 70 N or from about 37 N to about 62 N. In further specific embodiments, however, the two springs may produce different forces with a first spring having a force selected within the range of from about 80 N to about 120 N, and a second spring having a force selected within the range of from about 40 N to about 80 N.

The two potential energy storage units, especially when in the form of spring such as a spiral spring may be made of a suitable elastic material, such as metal, for example, steel, copper, beryllium-copper alloys, nickel alloys, especially nickel-chromium alloys, such as Inconel®, or from another material, for example, a polymeric or ceramic material, such as, for example, zirconia oxide or aluminum oxide or rubber, for example rubber springs. In specific embodiments, the two potential energy storage units may be preferably made from the same material or may be made from two different materials.

In some embodiments, the at least two exit areas of the inhalation device each eject the first liquid composition and the second liquid composition along respective ejection trajectories. In some embodiments, the first exit area and the second exit area are incorporated into a single nozzle, or the first exit area is incorporated into a first nozzle and the second exit area is incorporated into a second nozzle. In some embodiments, the first exit area comprises at least two channels to eject the first liquid composition from the device and the second exit area comprises at least two channels to eject the second liquid composition from the device. In some particular embodiments, the first liquid composition is ejected from at least two ejection channels, each having its own ejection trajectory, and the second liquid composition is ejected from at least two ejection channels, each having its own ejection trajectory and independent of the ejection channels of the first liquid composition, for a total of at least four exit areas for one inhaler device. In some particular embodiments, for each liquid composition, the at least two ejection channels may be oriented at angles such that at least two of said ejection trajectories intersect with one another at a collision point, such that a collision-type (or impingement-based) aerosol formation is achieved.

In some preferred embodiments, the exit areas and/or nozzles are adapted to separately eject the first liquid composition and the second liquid composition to avoid any interference, undesired chemical interactions, or precipitation of the potentially incompatible components (e.g., active ingredients, additives, and/or excipients) of the liquid compositions. In some embodiments, the first liquid composition is ejected from one ejection channel having its own ejection trajectory, i.e., a direction along which the respectively emitted liquid stream leaves its channel, and the second liquid composition is ejected from another ejection channel having its own ejection trajectory. Alternatively, the first liquid composition is ejected from at least two ejection channels each having its own ejection trajectory, and the second liquid composition is ejected from at least two ejection channels each having its own ejection trajectory. In preferred embodiments, the exit areas and/or nozzles are configured such that no interference of the aerosol streams of the at least two liquid compositions occur upon ejection from the device.

In specific embodiments, the inhalation device according to the present invention may be to about-mist-inhaler (SMI) wherein the term "soft-mist-inhaler" as used herein, refers to a preferably non-electrified mobile inhalation device for liquid formulations with low velocity nebulization properties. In further specific embodiments, such inhalation device or, more specifically, such soft-mist-inhaler comprises at least one impingement-type nozzle as described above for the nebulization/aerosolization of the medically active liquids to be administered.

Accordingly, in further specific embodiments, the inhalation device according to the present invention is a soft-mist inhaler and comprises at least two or, more specifically two impingement-type nozzles as described above, each impingement-type nozzle having two ejection channels with two corresponding ejection trajectories, wherein the two ejection trajectories of one impingement-type nozzle have one collision point in which the two ejection trajectories intersect. In further specific embodiments, each of the at least two liquid compositions or, more specifically, of the first and the second liquid compositions is dispensed or ejected by a separate impingement-type nozzle as described above.

Preferably, the inhalation device according to the invention and the embodiments described herein releases a metered dose each of the first and second liquid compositions upon actuation, each metered dose having the same or different volume and is at least about 1 μL (microliter). In further embodiments, each of the metered doses of the first and second liquid composition released upon actuation of the inhalation device may have the same or different volume and is at least about 1 μL, 2 μL, 5 μL, 10 μL, or 15 μL, or at least about 20 μL, 25 μL, 30 μL, or 50 μL. In other embodiments, each of the metered doses of the first and second liquid compositions released upon actuation may have the same or different volume and is about 1 μL to about 50 μL, or about 5 to about 30 μL, or about 10 to about 20 μL. In some embodiments, each of the metered doses of the first and second liquid compositions released upon actuation has a volume of about 1 μL. In other embodiments, each of the metered doses of the first and second liquid compositions released upon actuation has a volume of about 10 μL. In yet other embodiments, each of the metered doses of the first and second liquid compositions released upon actuation has a volume of about 15 μL.

In another embodiment of the invention, a single dose of the first liquid composition and the second liquid composition may be released by a one (single) actuation, or a plurality of actuations of the inhalation device.

Preferably each of the single doses of the first liquid composition and the second liquid composition may have the same or different mass and comprises an amount of at least about 0.1 μg (microgram), such as from about 0.1 μg to about 1.000 μg, or from about 1 μg to about 250 μg, or from about 1 μg to about 50 μg of a first active ingredient and at least about 0.1 μg, such as from about 0.1 μg to about 1.000 μg, or from about 1 μg to about 250 μg or from about 1 μg to about 50 μg of a second active ingredient. In other embodiments, the first liquid composition comprises a first active ingredient and the second liquid composition comprises a second active ingredient that may have the same or different mass and comprises an amount of at least 1 μg, 2 μg, 2.5 μg, 5 μg, 10 μg, 20 μg, 50 μg, or 100 μg. In yet further embodiments, the single dose of the first liquid composition comprises an amount of a first active ingredient and the second liquid composition comprises an amount of a second active ingredient and optionally a third active ingredient that may have the same or different mass in the range of about 1 to 10 μg, about 2 to 30 μg, or about 2.5 to 25 μg.

In further embodiments, the first and/or the second liquid composition, as the case may be, may comprise more than one active ingredient, such as a mixture of two or more different active ingredients in the amounts or concentrations, as described above.

In a further embodiment, the inhalation device can be held comfortably with one hand. The inhalation device comprises at least two reservoirs for separately storing the first and second liquid compositions, and at least two pumping units each comprising a pumping chamber for generation of a pressure inside said pumping chamber, wherein the first pumping chamber is fluidically connected with the first reservoir, optionally by means of a first reservoir pipe (or reservoir pipe section), via a first check valve, which blocks in the direction of the first reservoir. Similarly, the second pumping chamber is fluidically connected with the second reservoir, optionally by means of a second reservoir pipe (or reservoir pipe section), via a second check valve, which blocks in the direction of the second reservoir. Thus, the first and second check valves allow a liquid flow from the first and second reservoirs into the first and second pumping chambers and block a flow in the opposite direction.

In some embodiments, the inhalation device further comprises a first riser pipe having at least one reservoir-facing, interior end which can be received in the first pumping chamber, and a first exit area, which is connected liquid-tight directly or indirectly to the exterior end of the first riser pipe. Similarly, the inhalation device further comprises a second riser pipe having at least one reservoir-facing, interior end which can be received in the second pumping chamber, and a second exit area, which is connected liquid-tight directly or indirectly to the exterior end of the second riser pipe.

In some embodiments, the interior volume of the at least two pumping chambers are changeable by means of relative motion of the pumping chamber to the riser pipes in that each riser pipe increases the volume by being pushed into and decreases the volume by being pulled out of its respective pumping chamber. The term "interior volume" describes the volume which extends from the reservoir-facing inlet of each pumping chamber to the place where the interior end of the respective riser pipe is located.

In another embodiment of the invention, each riser pipe is immobile and firmly, directly or indirectly, and/or permanently or detachably, attached to the device, while each pumping chamber is movable relative to the device. In other words, each riser pipe maintains its position relative to the device, and each pumping chamber can alter its position relative to the device, and in particular, along a longitudinal axis of the same, such as to perform a piston-in-cylinder-type movement of the immobile riser pipe in the movable pumping chamber. Such an immobile riser pipe is described in detail in WO2018/197730 which is herein incorporated by reference in its entirety.

In another embodiment, the immobility of each riser pipe is primarily related to the exit area, rather than to the device. Thus, exit areas and riser pipes form—in terms of movability—one unit. However, if the exit areas itself are immobile with respect to the device, this is also true for the riser pipes, thus arriving at the described embodiment.

An advantage of these features is that the passages between pumping chambers and reservoirs can be designed with less restrictions compared to the known art. It is, for example possible to design a significantly larger check valve, which is easier to manufacture, since it does not have to be contained within the hollow piston known from the art. As a result, the size of the respective check valve is mainly only restricted by the interior size of the device or, if such a construction is desired, the inner size of a potential energy storage unit that surrounds the pumping units. The (approximate) identity of the diameter of valve, riser pipe and reservoir pipe, as known from the art, becomes obsolete. Furthermore, since no movable piston needs to be connected to each of the respective reservoirs, the component which enters the reservoirs and the movable component (i.e., the pumping chambers) can be designed independent of each other, allowing to better suit the individual functions. In this respect, the invention provides for higher design flexibility because the at least two movable pumping chambers, due to their robust structure and dimensions, provide better opportunities for designing a mechanically stable connection with the reservoirs than does the respective movable riser pipe which is typically less robust. Also, the connection between pumping chambers and reservoirs can be designed with a larger diameter, such that higher flow velocities and fluid viscosities become feasible. Further, a mechanical support for the reservoirs can be integrated into the component that comprises the pumping chambers. Additionally, the vent for pressure equilibration of the reservoirs can be moved away from the reservoir body itself to, e.g., a connector which forms an interface between reservoirs and pumping chambers, facilitating the construction and avoiding the necessity to provide an essentially "open" reservoir body.

According to one embodiment, each of the at least two check valves is adapted to open only when the pressure difference between the upstream and the downstream side of the valve, i.e., the reservoir and the pumping chamber side, is above a predefined threshold value, and remains closed as long as the pressure difference is below the threshold value. "Pressure difference" means that, irrespective of the concrete pressure values, only the relative pressure difference between the two sides is relevant for determining whether the check valve blocks or opens.

Upon activation of each of the at least two pumping units, by building up a high pumping chamber pressure, the pressure difference (due to a high pressure in the pumping chamber, and a significantly lower pressure in the reservoir, resulting in a large pressure difference) becomes high enough and exceeds the threshold value of the pressure difference, so that each of the at least two check valves finally opens and allows the pressure chamber being filled with liquid from the reservoir.

According to a further embodiment, an inhalation device comprises at least two outlet valves, one inside each of the at least two riser pipes for avoiding a return flow of liquid or air into the exterior end of the same.

According to another embodiment, the inhalation device comprises at least two outlet valves between each of the at least two riser pipes and at least two exit areas for avoiding a return flow of liquid or air towards the exterior end of each of the at least two riser pipes.

Optionally, each of the at least two outlet valves can be of a type that blocks below (and opens above) a threshold pressure difference as described above.

In some embodiments, the first exit area and the second exit are incorporated into a single nozzle, or the first exit area is incorporated into a first nozzle and the second exit area is incorporated into a second nozzle in order to separate the two exit streams of the first and second liquid compositions. In particular embodiments, the nozzle(s) is constructed as a stack of relatively flat plates. Such plates can preferably be fabricated by material subtracting technologies such as etching or the like. Wafers of different materials such as silicon, glass, metal, ceramics, or plastics can form the semi-finished product. The channels leading to each exit area are brought into one of the two flat sides of the substrate, or even on both sides. Then, by stacking several of such plates, a nozzle stack providing a plurality of ejection channel pairs can be fabricated. In some embodiments, each exit area comprises at least two channels to eject the liquid compositions from the device.

In other embodiments, the nozzle(s) is constructed from a three-dimensional rotation symmetric basic shape. Such a basic shape can be a cone, a cylinder, or a pyramid. Typically, the rotation or symmetry axis of the base shape coincides with the main axis of the finished nozzle.

According to a further embodiment, each of the at least two reservoirs are firmly attached to the pumping chamber and thus movable inside the device. This means that in each ejection cycle, the first reservoir moves together with the first pumping chamber from the initial position, in which the first pumping chamber has its maximum interior volume, to the end position, in which the same is minimal, and eventually back to the initial position. Similarly, the second reservoir moves together with the second pumping chamber from the initial position, in which the second pumping chamber has its maximum interior volume, to the end position, in which the same is minimal, and eventually back to the initial position. As used herein, the expression "firmly attached" includes both permanent and non-permanent (i.e., releasable) forms of attachment. One of the advantages of this construction is that it provides the smallest possible dead volume between reservoirs and pumping chambers.

According to another embodiment, each of the at least two reservoirs is connected to the at least one pumping chamber by means of a flexible element such as e.g., a hose, and firmly attached to the device. Thus, according to this embodiment, each of the first and second reservoirs does not move along with the first and second pumping chambers, but is firmly (but, however, typically detachably) attached to the device. One advantage of this construction is that the energy which is abruptly released upon unlocking the means for the storage of potential energy acts solely onto the first and second pumping chambers for accelerating the same, but not also onto the first and second reservoirs which typically—and in particular at the beginning of its usage—can have a relatively large mass. A higher acceleration of the first and second pumping chambers, and thus, a higher pressure, is the result.

In another aspect, the present invention relates to a first reservoir containing a first liquid composition comprising one or more active ingredients, additives, and/or excipients, and a second reservoir containing a second liquid composition comprising one or more active ingredients, additives, and/or excipients, wherein each of the first and second reservoirs is adapted for use with an inhalation device according to the first aspect of the invention, or combination of device embodiments described above. The first and second reservoirs are adapted to be housed and integrated with the other features and components of the inhalation device and may be standardized where a plurality of reservoirs (e.g., two or greater than two) may be contained and integrated in the inhalation device. Said first reservoir is connectable to the first pumping chamber, and said second reservoir is connectable to the second pumping chamber. In one embodiment, each of the reservoirs (2A, 2B) according to the invention is adapted to be firmly attachable to each of the pumping chambers (3A, 3B) and is thus movable inside the device. In an alternative embodiment, each of the reservoirs (2A, 2B) is adapted to connect to each of the pumping chamber (3A, 3B) by means of a flexible element, and firmly attached to the device.

The amount of the first and second liquid compositions which may be accommodated, i.e., stored in the first and second reservoirs is an amount whereby on actuation of the device, an amount of at least one metered dose of the first and second liquid compositions is released. In some embodiments, each of the first and second reservoir is a multi-dose reservoir, meaning that it contains a plurality of single doses, which may be administered via a plurality of actuations of the device. Alternatively expressed, each of the first and second reservoirs preferably contains an amount of the first and second liquid compositions adapted for multiple, or a plurality of actuations of the inhalation device.

In one embodiment, the inhalation device and/or the at least two reservoirs adapted for the inhalation device contains an amount of at the least two liquid compositions suitable for 1 to about 120, or 1 to about 90, or 1 to about 60, or 1 to about 30, or 1 to about 20, or from about 10 to about 90 or to about 60 actuations of the inhalation device, or an amount of at least two liquid compositions suitable for the release of 1 to 120, or 1 to 90, or 1 to 60, or 1 to 30, or 1 to 20, or from about 10 to about 60 or to about 80 metered doses of aerosolized liquid compositions.

In a further aspect of the present invention, the inhaler device includes a first liquid composition in a first reservoir and a second liquid composition in a second reservoir. The first and second liquid compositions are formulated as compositions that are suitable, and adapted for inhalative use, in other words compositions that may be atomized for inhalation and that are physiologically acceptable for inhalation by a subject.

The first and second liquid compositions contained within the inhalation device, and, more specifically, within the first and second reservoirs may be in the form of a dispersion, for example a suspension with a liquid continuous phase, and a solid dispersed phase. Preferably, however, the first and second liquid compositions are in the form of a solution, where active ingredients and other materials are dissolved and solubilized in a liquid carrier solution.

In some embodiments, the first and the second liquid compositions comprise the same or different solvent compositions as liquid carriers. In specific embodiments, however, the first and the second liquid compositions preferably comprise different solvent compositions as liquid carriers. For example, the first liquid composition and second liquid composition may both comprise an aqueous solution. In other embodiments, the first liquid composition may comprise an aqueous solution, and the second liquid composition may comprise an organic solution or a mixture of aqueous and organic solutions. In some embodiments, the organic solution comprises an alcoholic solution, such as an ethanolic solution.

In further specific embodiments, the liquid carrier or solvent comprises water and/or ethanol, preferably ethanol. In further specific embodiments, such liquid carrier or solvent comprises or preferably consists of ethanol or a mixture of ethanol and water, wherein the ethanol may be comprised in an amount of at least about 50 wt.-%, or at least about 60 wt.-% or at least about 70 wt.-% or even more and water in a corresponding amount of up to about 50 wt.-%, or up to about 40 wt.-% or up to about 30 wt.-% or less. In specific embodiments, the liquid vehicle or solvent comprises or consists of ethanol in an amount of about 60 to about 80 wt.-%, such as about 70 wt.-%, and water in an amount of about 40 to about 20 wt.-%, such as about 30 wt.-%.

In some embodiments, the first liquid composition comprises a long-acting beta agonist (LABA), preferably in a pharmaceutically effective amount. Non-limiting, exemplary long-acting beta agonists include albuterol, arformoterol, bambuterol, bitolterol, broxaterol, carbuterol, clenbuterol, fenoterol, formoterol, hexoprenaline, ibuterol, indacaterol, indacterol, isoetharine, isoprenaline levosalbutamol, mabuterol meluadrine, metaproterenol, olodaterol, orciprenaline, pirbuterol, procaterol, reproterol, rimiterol, ritodrine, salmeterol, salmefamol, soterenot, sulphonterol, tiaramde, terbutaline, and terbuterol. In some embodiments, the long-acting beta agonist is olodaterol.

In other embodiments, the first liquid composition comprises a long-acting muscarinic antagonist (LAMA), preferably in a pharmaceutically effective amount. Non-limiting, exemplary long-acting muscarinic antagonists include aclidinium bromide, glycopyrronium bromide, revefenacin, tiotropium, such as tiotropium bromide, umeclidinium bromide, oxitropium bromide, flutropium bromide, ipratropium bromide, trospium chloride, and tolterodine. In some embodiments, the long-acting muscarinic antagonist is tiotropium bromide.

In some embodiments, the first liquid composition comprises a mixture of a long-acting beta agonist and a long-acting muscarinic antagonist. In some embodiments, the mixture of the long-acting beta agonist and long-acting muscarinic antagonist comprises olodaterol and tiotropium bromide.

In some embodiments, the second liquid composition comprises an inhaled corticosteroid (ICS). Non-limiting, exemplary inhaled corticosteroids include prednisolone, prednisone, butixocort propionate, flunisolide, beclomethasone, triamcinolone, budesonide, fluticasone, mometasone (furoate), ciclesonide, rofleponide, dexamethasone, etiprednol-dichloroacetat, deflazacort, etiprednol, loteprednol, RPR-106541, NS-126, and ST-26. In some embodiments, the inhaled corticosteroid is ciclesonide.

In some embodiments, the first liquid composition comprises a long-acting beta agonist and the second liquid composition comprises an inhaled corticosteroid. In specific embodiments, the long-acting beta agonist is olodaterol and the inhaled corticosteroid is ciclesonide.

In some embodiments, the first liquid composition comprises a mixture of a long-acting beta agonist and a long-acting muscarinic antagonist and the second liquid composition comprises an inhaled corticosteroid. In specific embodiments, the mixture of the long-acting beta agonist and long-acting muscarinic antagonist comprises olodaterol and tiotropium bromide and the inhaled corticosteroid is ciclesonide.

In further embodiments, the first and second liquid compositions may comprise, optionally, one or more physiologically acceptable additives and/or excipients, which are suitable for inhalative use. Excipients which may be featured in the composition include, but are not limited to, one or more buffering agents to regulate or control pH of the solution, salts, taste-masking agents, surfactants, lipids, antioxidants, preservatives, such as benzalkonium chloride (BAC), parabens such as methylparaben, ethylparaben, propylparaben, sodium benzoate, sorbic acid and salts thereof, and co-solvents, which may be used to enhance or improve solubility, for example ethanol, or a glycol. In some embodiments, the liquid compositions are also essentially free of a propellant such as a hydrofluoroalkane (HFA) propellant.

A further aspect of the present invention relates to the use of the inhalation device in therapy and prophylactic treatment of a disease or condition. In specific embodiments, the disease or condition is a lung or respiratory disease or condition. In particular, the inhalation device according to the invention is used for the treatment or prevention of a lung disease or condition. As understood herein, a lung disease or condition may affect one or more anatomical aspect and/or function of a subject's lung(s) and associated respiratory airways.

Treatment refers to the administration of the first and second liquid compositions for the therapy of the disease or condition, for example leading to ameliorating, decreasing, or relieving of at least one symptom of the disease or condition, or stopping or slowing the progression of at least one symptom of the disease or condition, such as, for example, preserving lung function. The prevention of a disease or condition may be understood to be prophylactic treatment and refers to the administration of the first and second liquid compositions to a subject that may not have developed the disease or condition but is at risk, or susceptible to the disease or condition.

In both the treatment or prevention of the disease or condition, the first and second liquid compositions are administered by means of the inhalation device and embodiments described herein at therapeutically effective amounts, such as in the amounts described above.

In a particularly preferred embodiment, the disease or condition is a lung disease such as, for example, asthma or chronic obstructive pulmonary disease ("COPD").

In a further aspect, the present invention provides for the use of an inhalation device or reservoirs containing the first and second liquid compositions, as described in any one of the above embodiments, in the manufacture or preparation of a medicament or medical device for the treatment of a subject in need thereof in relation to any disease or condition is also provided for in the context of the present invention. In particular embodiments, the disease or condition is a lung disease or condition, for example, asthma or chronic obstructive pulmonary disease ("COPD"). In other particular embodiments, the first liquid composition comprises a long-acting beta agonist, such as olodaterol and the second liquid composition comprises an inhaled corticosteroid, such as ciclesonide. In yet other particular embodiments, the first liquid composition further comprises a long-acting muscarinic antagonist, such as tiotropium bromide.

In yet a further aspect, the present invention relates also to a method of treating or preventing a disease or condition in a subject in need thereof, the method comprising a step of administering a metered dose of a first liquid composition and a second liquid composition using an inhalation device as described in any one or combination of the above embodiments. In particular embodiments, the disease or condition is a lung disease or condition, for example, asthma or chronic obstructive pulmonary disease ("COPD"). In other particular embodiments, the first liquid composition comprises a long-acting beta agonist, such as olodaterol and the second liquid composition comprises an inhaled corticosteroid, such as ciclesonide. In yet other particular embodiments, the first liquid composition further comprises a long-acting muscarinic antagonist, such as tiotropium bromide.

Preferably the inhalation device used in the methods described herein is a handheld, i.e., portable device, whereby the administration of the first and second liquid compositions and actuation of the device is carried out by the human subject or patient themselves directly and in accordance with prescribed instructions which may also accompany the device.

In a further aspect, the invention provides a method for delivering liquid compositions to a subject in need thereof, the method comprising the step of providing an inhalation device as described above to said subject. The subject is preferably a human patient, in particular a human patient suffering from a disease or condition, preferably a lung disease, such as asthma or COPD. The patient may further be provided with instructions to use the device, to actuate it and to inhale the aerosol emitted from it.

In yet a further aspect, the invention provides a method of treating a subject suffering from a disease or condition, preferably a lung disease, such as asthma or COPD, the method comprising a step of administering a first and second liquid composition to said subject using a device as described above. Again, the patient may be provided with instruction to use the device, to actuate it, and to inhale the aerosol emitted from it.

In yet a further aspect, the present invention provides for the combination of a first and a second liquid composition for use in a method of treating a subject suffering from a disease or condition, preferably a lung disease, such as asthma or COPD, wherein the first and the second liquid composition is administered to the subject using an inhalation device according to the first aspect of the invention.

DESCRIPTION OF THE DRAWINGS

FIG. 1 shows the main components of an inhalation device useful for carrying out the invention.

In FIG. 1, the main components of an exemplary inhalation device useful for carrying out the invention are depicted schematically and not-to-scale, at the situation prior to first use. The depicted device represents a non-limiting embodiment of the inhalation devices of the present invention disclosed herein.

The inhalation device comprises a housing 1, which is preferably shaped and dimensioned such that it can be held with one hand and can be operated by one finger, e.g., the thumb (not shown). The device further comprises two reservoirs 2A, 2B for the respective storage of a medically active liquid F1, F2. The depicted reservoirs 2A, 2B are designed to be collapsible; that means that during proceeding emptying, the elastic or at least limp walls buckle, so that the relative negative pressure (i.e., partial vacuum) which is necessary for extraction of a certain amount of liquid F1, F2 is not, or almost not, increased. A similar effect can be achieved via alternative embodiments, in which a rigid container has a movable bottom by means of which the interior volume of the respective reservoir can also be successively be reduced (not shown).

Further, the inhalation device comprises a pumping unit with two pumping chambers 3A, 3B for generation of the desired pressures which are necessary for emitting liquid F1, F2 and nebulizing the same. The pumping unit can also comprise additional components that are not depicted (push button, locking device, etc.).

At least two potential energy storage units 6A, 6B (e.g., springs) are provided, each of which is coupled with one (upwards directed) end to the pumping chambers 3A, 3B and which is supported at housing 1 (lower part of the FIGURE).

The inhalation device further comprises at least two riser pipes 4A, 4B with at least one respective reservoir-facing, interior end 4A', 4B' which can be received in said pumping chambers 3A, 3B. In other words, riser pipes 4A, 4B can at least partially be pushed into pumping chambers 3A, 3B, resulting in a decrease of the interior volumes of pumping chambers 3A, 3B. The term "interior volume" describes that volume which extends from the reservoir-facing inlet of the pumping chamber 3A, 3B to the place where the interior end 4A', 4B' of the riser pipe 4A, 4B is located.

Preferably, in the section which serves for the reception of the riser pipes, pumping chamber 3A, 3B has section with a circular inner cross section that corresponds to the (then also) circular outside cross section of the according riser pipe section. Of course, other cross section shapes are possible as well.

Further, the inhalation device comprises two exit areas 5A, SB, each of which is connected liquid-tight to the respective exterior ends 4A", 4B" of riser pipes 4A, 4B. Exit areas 5A, 5B are suitable for nebulizing/atomizing liquid in a single stream or at least two streams by using the principle of two colliding liquid jets. Exit areas 5A, 5B which are depicted as an example comprises two separate nozzle units, but the exit areas 5A, 5B may also be included in one nozzle unit (not depicted). Each of the two exit areas 5A, 5B is connected to an individual pumping chamber 3A, 3B and thus, liquid reservoirs 2A, 2B. Each liquid F1, F2 has its own pumping chamber 3A, 3B in order to avoid undesired mixing.

Riser pipes 4A, 4B are designed to be immobile and firmly attached to the device. Riser pipes 4A, 4B are also firmly attached to exit areas 5A, 5B, which in turn are attached to the device as well. On the contrary, pumping chambers 3A, 3B are designed to be movable with respect to the device and exit areas 5A, 5B. The benefits of this design have already been explained; reference is made to the respective sections above.

Item List

Amongst others, the present invention relates to the following specific embodiments:

1. An inhalation device for the generation of an aerosol of at least two liquid compositions, the device comprising at least a first and second reservoir (2A, 2B) containing at least a first and a second liquid composition (F1, F2), wherein the inhalation device is a pump-actuated inhaler adapted to release upon actuation a metered dose of the first liquid composition (F1) from the first reservoir (2A) and a metered dose of the second liquid composition (F2) from the second reservoir (2B), wherein the inhalation device comprises a first and second reservoir (2A, 2B) for storing the first and second liquid composition (F1, F2) fluidically connected to at least a first and second pumping chamber (3A, 3B) for generation of a first pressure inside said first pumping chamber (3A) and a second pressure inside said second pumping chamber (3B), a first and second riser pipe (4A, 4B), each of which can be received with a reservoir-facing, interior end (4A', 4B') in said first and second pumping chamber (3A, 3B), wherein the interior volume of the first and second pumping chamber (3A, 3B) is changeable by means of relative motion of the first and second pumping chamber (3A, 3B) to the first and second riser pipe (4A, 4B), at least a first exit area and a second exit area (5A, 5B) adapted to separately eject the first and second liquid composition (F1, F2) from the inhalation device, a first potential energy storage unit (6A) coupled with one end of the first pumping chamber (3A), and a second potential energy storage unit (6B) coupled with one end of the second pumping chamber (3B).
2. The inhalation device according to embodiment 1, wherein the first and second pumping chamber (3A, 3B) coupled to a separate potential energy storage unit (6A, 6B) generates a desired pressure for releasing the at least two liquid compositions.
3. The inhalation device according to any one of embodiments 1 to 2, wherein each of the first and second riser pipe (4A, 4B) is immobile and firmly attached to the device and/or to the first and second exit area (5A, 5B), and each of the first and second pumping chamber (3A, 3B) is movable relative to the device and/or to the first and second exit area (5A, 5B).
4. The inhalation device according to any one of embodiments 1 to 3, wherein the first potential energy storage unit (6A) and the second potential energy storage unit (6B) each produce the same force.
5. The inhalation device according to any one of embodiments 1 to 3, wherein the first potential energy storage unit (6A) and the second potential energy storage unit (6B) each produce a different force.
6. The inhalation device according to embodiment 4 or 5, wherein the force is about 5 newtons (N) to about 200 newtons (N).
7. The inhalation device according to any one of embodiments 1 to 6, wherein the first potential energy storage unit (6A) and the second potential energy storage unit (6B) each comprise a spring.

8. The inhalation device according to claim 7, wherein each spring has the same or different spring rate (k) from about 50 newtons/meter (N/m) to about 5.000 newtons/meter (N/m).

9. The inhalation device according to any one of embodiments 1 to 8, wherein the first exit area (5A) and the second exit area (5B) are incorporated into a single nozzle.

10. The inhalation device according to any one of embodiments 1 to 8, wherein the first exit area (SA) is incorporated into a first nozzle and the second exit area (5B) is incorporated into a second nozzle.

11. The inhalation device according to any one of embodiments 1 to 10, wherein the first exit area (5A) comprises at least two channels to eject the first liquid composition (F1) from the device and the second exit area (5B) comprises at least two channels to eject the second liquid composition (F2) from the device.

12. The inhalation device according to any one of embodiments 1 to 11, wherein the first reservoir and the second reservoir are incorporated into a single cartridge unit or the first reservoir is incorporated into a first cartridge unit and the second reservoir is incorporated into a second cartridge unit.

13. The inhalation device according to any one of embodiments 1 to 12, wherein the metered dose of the first liquid composition (F1) has the same volume than the metered dose of the second liquid composition (F2).

14. The inhalation device according to any one of embodiments 1 to 12, wherein the metered dose of the first liquid composition (F1) has a different volume than the metered dose of the second liquid composition (F2).

15. The inhalation device according to any one of embodiments 1 to 14, wherein the first liquid composition (F1) and the second liquid composition (F2) comprise the same or different solvent compositions.

16. The inhalation device according to embodiment 15, wherein the first liquid composition (F1) comprises an aqueous solution and the second liquid composition (F2) comprises an organic solution or a mixture of aqueous and organic solutions.

17. The inhalation device according to embodiment 16, wherein the organic solution comprises an alcoholic solution.

18. The inhalation device according to any one of embodiments 1 to 17, wherein the first liquid composition comprises a long-acting beta agonist and the second liquid composition comprises an inhaled corticosteroid.

19. The inhalation device according to embodiment 18, wherein a metered dose of the first liquid composition comprising the long-acting beta agonist has a volume of at least 1 μL and a metered dose of the second liquid composition comprising the inhaled corticosteroid has a volume of at least 1 μL.

20. The inhalation device according to embodiment 19, wherein the metered dose of the first liquid composition comprises an amount of at least 1 μg of the long-acting beta agonist, and wherein the metered dose of the second liquid composition comprises an amount of at least 1 μg of the inhaled corticosteroid.

21. The inhalation device according to any one of embodiments 18 to 20, wherein the first liquid composition comprises a mixture of a long-acting beta agonist and a long-acting muscarinic antagonist and the second liquid composition comprises an inhaled corticosteroid.

22. The inhalation device according to embodiment 21, wherein a metered dose of the first liquid composition comprising the long-acting beta agonist and long-acting muscarinic antagonist has a volume of at least 1 μL and a metered dose of the second liquid composition comprising the inhaled corticosteroid has a volume of at least 1 μL.

23. The inhalation device according to embodiment 22, wherein the metered dose of the first liquid composition comprises an amount of at least 1 μg of the long-acting beta agonist and an amount of at least 1 μg of the long-acting muscarinic antagonist, and wherein the metered dose of the second liquid composition comprises an amount of at least 1 μg of the inhaled corticosteroid.

24. The inhalation device according to any one of embodiments 18 to 23, wherein the long-acting beta agonist is selected from the group consisting of albuterol, arformoterol, bambuterol, bitolterol, broxaterol, carbuterol, clenbuterol, fenoterol, formoterol, hexoprenaline, ibuterol, indacaterol, indacterol, isoetharine, isoprenaline levosalbutamol, mabuterol meluadrine, metaproterenol, olodaterol, orciprenaline, pirbuterol, procaterol, reproterol, rimiterol, ritodrine, salmeterol, salmefamol, soterenot, sulphonterol, tiaramde, terbutaline, and terbuterol.

25. The inhalation device according to any one of embodiments 18 to 24, wherein the long-acting beta agonist is olodaterol.

26. The inhalation device according to any one of embodiments 21 to 25, wherein long-acting muscarinic antagonist is selected from the group consisting of aclidinium bromide, glycopyrronium bromide, revefenacin, tiotropium bromide, umeclidinium bromide, oxitropium bromide, flutropium bromide, ipratropium bromide, trospium chloride, and tolterodine.

27. The inhalation device according to any one of embodiments 21 to 26, wherein long-acting muscarinic antagonist is tiotropium bromide.

28. The inhalation device according to any one of embodiments 18 to 27, wherein the inhaled corticosteroid is selected from the group consisting of prednisolone, prednisone, butixocort propionate, flunisolide, beclomethasone, triamcinolone, budesonide, fluticasone, mometasone, ciclesonide, rofleponide, dexamethasone, etiprednol-dichloroacetat, deflazacort, etiprednol, loteprednol, RPR-106541, NS-126, and ST-26.

29. The inhalation device according to any one of embodiments 18 to 28, wherein the inhaled corticosteroid is ciclesonide.

30. The inhalation device according to any one of embodiments 21 to 29, wherein the long-acting muscarinic antagonist is tiotropium bromide, the long-acting beta agonist is olodaterol, and the inhaled corticosteroid is ciclesonide.

31. The inhalation device according to any one of embodiments 1 to 30, wherein the first reservoir (2A) is firmly attached to the first pumping chamber (3A) and the second reservoir (2B) is firmly attached to the second pumping chamber (3B) and thus movable inside the device; or wherein the first reservoir (2A) is connected to the first pumping chamber (3A) with a first flexible element and the second reservoir (2B) is connected to the second pumping chamber (3B) with a second flexible element, and wherein the first and second reservoirs (2A, 2B) are each firmly attached to the device.

32. The inhalation device according to any one of embodiments 1 to 31, wherein each of the first liquid composition and the second liquid composition further comprises one or more excipients, buffering agents, and/or co-solvents.

33. The inhalation device according to any one of embodiments 1 to 32, for use in the treatment or prevention of disease or condition.
34. The inhalation device according to any one of embodiments 1 to 33, for use in the treatment or prevention of a lung disease or condition.
35. The inhalation device of embodiment 34, wherein the lung disease or condition is asthma or chronic obstructive pulmonary disease ("COPD").
36. The inhalation device of any one of embodiments 18 to 35, wherein the long-acting beta agonist is dissolved in the first liquid composition, and the inhaled corticosteroid is dissolved in the second liquid composition.
37. The inhalation device of embodiment 36, wherein the first liquid composition further comprises a long-acting muscarinic antagonist dissolved in the first liquid composition.
38. A method of treating a subject suffering from a disease or condition, the method comprising a step of administering an effective amount of at least two active ingredients to said subject using a device according to any one of embodiments 1 to 37.
39. The method of embodiment 38, wherein the disease or condition is a lung disease or condition.
40. The method of according to any one of embodiments 38 to 39, wherein the at least two active ingredients comprise a long-acting beta agonist and an inhaled corticosteroid.
41. The method of embodiment 40, wherein the at least two active ingredients comprise a long-acting beta agonist, a long-acting muscarinic antagonist, and an inhaled corticosteroid.
42. The method according to any one of embodiments 39 to 41, wherein the lung disease or condition is asthma or chronic obstructive pulmonary disease ("COPD").
43. A method of treating a subject suffering from a disease or condition, the method comprising a step of administering an effective amount of at least two liquid compositions each comprising an active ingredient to said subject using a device according to any one of embodiments 1 to 37.
44. A method for delivering at least two liquid compositions to a subject in need thereof, comprising the step of providing an inhalation device according to any one of embodiments 1 to 37 to said subject.
45. The method according to any one of embodiments 43 to 44, wherein the at least two liquid compositions comprise a long-acting beta agonist and an inhaled corticosteroid.
46. The method of embodiment 45, wherein the at least two liquid compositions comprise a first liquid composition comprising a long-acting beta agonist and a long-acting muscarinic antagonist and a second liquid composition comprising an inhaled corticosteroid.
47. A first reservoir containing a first liquid composition comprising a long-acting beta agonist and a second reservoir containing a second liquid composition comprising an inhaled corticosteroid, wherein the first and second reservoirs are adapted for use with an inhalation device according to any one of embodiments 1 to 37.
48. The reservoir of embodiment 47, wherein the first liquid composition further comprises a long-acting muscarinic antagonist.

LIST OF REFERENCES

1 housing
2A,2B first and second reservoirs
3A,3B first and second pumping chambers
4A,4B first and second riser pipes
4A',4B' interior end
4A",4B" exterior end
5A,5B first exit area and second exit area
6A,6B potential energy storage units
F1,F2 first and second liquid compositions

The invention claimed is:

1. An inhalation device for the generation of an aerosol of at least two liquid compositions, the device comprising at least a first and second reservoir containing at least a first and a second liquid composition, wherein the inhalation device is a pump-actuated inhaler adapted to release upon actuation a metered dose of the first liquid composition from the first reservoir and a metered dose of the second liquid composition from the second reservoir, wherein the first and second reservoir for storing the first and second liquid composition are fluidically connected to at least a first and second pumping chamber for generation of a first pressure inside said first pumping chamber and a second pressure inside said second pumping chamber, a first and second riser pipe, each of which is able to be received with a reservoir-facing, interior end in said first and second pumping chamber, wherein the interior volume of the first and second pumping chamber is changeable by means of relative motion of the first and second pumping chamber to the first and second riser pipe, at least a first exit area and a second exit area adapted to separately eject the first and second liquid composition from the inhalation device, a first potential energy storage unit coupled with one end of the first pumping chamber, and a second potential energy storage unit coupled with one end of the second pumping chamber, wherein the first and the second potential energy storge units are configured to separately generate the first and the second pressures, respectively, for releasing the at least two liquid compositions.

2. The inhalation device according to claim 1, wherein each of the first and second riser pipe is immobile and firmly attached to the device and/or to the first and second exit area, and each of the first and second pumping chamber is movable relative to the device and/or to the first and second exit area.

3. The inhalation device according to claim 1, wherein the first potential energy storage unit and the second potential energy storage unit each produce the same force.

4. The inhalation device according to claim 3, wherein the force is about 5 newtons (N) to about 200 newtons (N).

5. The inhalation device according to claim 1, wherein the first potential energy storage unit and the second potential energy storage unit each produce a different force.

6. The inhalation device according to claim 1, wherein the first potential energy storage unit and the second potential energy storage unit each comprise a spring.

7. The inhalation device according to claim 1, wherein the metered dose of the first liquid composition has a same volume as the metered dose of the second liquid composition.

8. The inhalation device according to claim 1, wherein the metered dose of the first liquid composition has a different volume than the metered dose of the second liquid composition.

9. The inhalation device according to claim 1, wherein the first liquid composition comprises a long-acting beta agonist and the second liquid composition comprises an inhaled corticosteroid.

10. The inhalation device according to claim 9, wherein the first liquid composition comprises a mixture of the long-acting beta agonist and a long-acting muscarinic antagonist and the second liquid composition comprises the inhaled corticosteroid.

11. The inhalation device according to claim 10, wherein the long-acting muscarinic antagonist is tiotropium bromide, the long-acting beta agonist is olodaterol, and the inhaled corticosteroid is ciclesonide.

12. The inhalation device according to claim 1, wherein the first exit area and the second exit area are incorporated into a single nozzle.

13. The inhalation device according to claim 1, wherein the first exit area is incorporated into a first nozzle and the second exit area is incorporated into a second nozzle.

14. The inhalation device according to claim 1, wherein the first reservoir and the second reservoir are incorporated into a single cartridge unit.

15. The inhalation device according to claim 1, wherein the first reservoir is incorporated into a first cartridge unit and the second reservoir is incorporated into a second cartridge unit.

16. The inhalation device according to claim 1, wherein the inhalation device is a soft-mist-inhaler.

17. The inhalation device according to claim 16, wherein the soft-mist inhaler comprises at least two impingement-type nozzles, each impingement-type nozzle having two ejection channels with two corresponding ejection trajectories, wherein the two ejection trajectories of one impingement-type nozzle have one collision point in which the two ejection trajectories intersect.

18. A method of treating or preventing a disease or condition in a subject in need thereof, the method comprising a step of administering the metered dose of the first liquid composition and the metered dose of the second liquid composition using the inhalation device according to claim 1.

19. The first reservoir containing the first liquid composition comprising a long-acting beta agonist and the second reservoir containing the second liquid composition comprising an inhaled corticosteroid, wherein the first and second reservoirs are adapted for use with the inhalation device according claim 1.

* * * * *